United States Patent
Lin et al.

(10) Patent No.: US 10,280,259 B2
(45) Date of Patent: May 7, 2019

(54) ALKYNYL MULTI-ARM POLYETHYLENE GLYCOL DERIVATIVE

(71) Applicant: JENKEM TECHNOLOGY CO., LTD. (BEIJING), Beijing (CN)

(72) Inventors: Meina Lin, Beijing (CN); Xiaomeng Chen, Beijing (CN)

(73) Assignee: JENKEM TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 15/170,905

(22) Filed: Jun. 1, 2016

(65) Prior Publication Data

US 2016/0271267 A1    Sep. 22, 2016

Related U.S. Application Data

(63) Continuation of application No. PCT/CN2014/092738, filed on Dec. 2, 2014.

(30) Foreign Application Priority Data

Dec. 2, 2013   (CN) .......................... 2013 1 0632776

(51) Int. Cl.
| | |
|---|---|
| *C08G 65/333* | (2006.01) |
| *C08G 65/332* | (2006.01) |
| *C08G 65/329* | (2006.01) |
| *C08G 65/331* | (2006.01) |
| *C08G 65/337* | (2006.01) |
| *A61K 47/60* | (2017.01) |
| *A61K 47/69* | (2017.01) |
| *A61K 9/06* | (2006.01) |
| *A61K 47/34* | (2017.01) |

(52) U.S. Cl.
CPC ........ *C08G 65/33324* (2013.01); *A61K 47/60* (2017.08); *A61K 47/6903* (2017.08); *C08G 65/329* (2013.01); *C08G 65/331* (2013.01); *C08G 65/332* (2013.01); *C08G 65/337* (2013.01); *C08G 65/3322* (2013.01); *C08G 65/33306* (2013.01); *C08G 65/33331* (2013.01); *C08G 65/33337* (2013.01); *A61K 9/06* (2013.01); *A61K 47/34* (2013.01); *C08G 2650/30* (2013.01); *C08G 2650/32* (2013.01); *C08G 2650/60* (2013.01); *C08L 2203/02* (2013.01)

(58) Field of Classification Search
None
See application file for complete search history.

(56) References Cited

PUBLICATIONS

Donahoe et al., Ultralow Protein Coating from Clickable PEG Nanogel Solutions: Benefits of Attachment under Salt-Induced Phase Separation Conditions and Comparison with PEG/Albumin Nanogel Coating. Langmuir, 2013, 29, 4128-4139.*
CAPLUS printout of "Donahoe et al., Ultralow Protein Coating from Clickable PEG Nanogel Solutions: Benefits of Attachment under Salt-Induced Phase Separation Conditions and Comparison with PEG/Albumin Nanogel Coating. Langmuir, 2013, 29, 4128-4139.".*

* cited by examiner

*Primary Examiner* — Po-Chih Chen
(74) *Attorney, Agent, or Firm* — Flener IP & Business Law, LLC; Zareefa B. Flener

(57) ABSTRACT

The present invention provides an alkynyl multi-arm polyethylene glycol derivative having a structure of a general formula I or general formula X VIII. In the derivative, X1, X2, X3 and X4 are linking groups, F1, F2, F3 and F4 are end groups, the end groups may be the same or may also be different, and are selected from: hydroxy, carboxyl, ester group, amino, alkynyl or the like, at least one of the end groups is alkynyl, and PEG is the same or different —$(CH_2CH_2O)_m$—, wherein m is an integer ranging from 3 to 250, and l is an integer greater than or equal to 1. The multi-arm polyethylene glycol derivatives have stronger application flexibility, and have good application prospect in aspects such as organic synthesis, medicine synthesis and medical instruments.

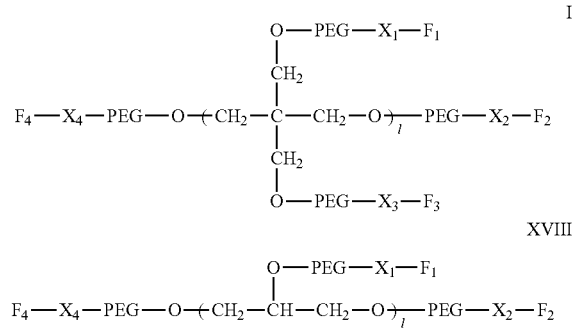

12 Claims, No Drawings

ALKYNYL MULTI-ARM POLYETHYLENE GLYCOL DERIVATIVE

CROSS-REFERENCE TO RELATED APPLICATION

The application is a continuation of PCT/CN2014/092738 (filed on Dec. 2, 2014), which claims priority from CN Patent Application Serial No. 201310632776.0 (filed on Dec. 2, 2013), the entire contents of which are incorporated herein by reference for all purposes.

FIELD OF THE INVENTION

The present invention relates to a polyethylene glycol active derivative, and more particularly to an multi-arm polyethylene glycol active derivative having an end group of alkynyl and a preparation method thereof.

BACKGROUND OF THE INVENTION

The polyethylene glycol is an extremely versatile polyether high molecular weight compounds, it can be used in many fields such as medicine, health, food, chemical, etc. Polyethylene glycol can be dissolved in water and many solvents and the polymer has excellent biocompatibility, can be dissolved in tissue fluid in vivo, can be rapidly excreted from the body without any toxic side effects.

In application of polyethylene glycol, end group plays a decisive role, different end groups of the polyethylene glycol has a different use. The polyethylene glycol polymeric chain segment is not limited to the terminal hydroxyl group, polyethylene glycol active derivative obtained through the introduction of other functionalized end groups such as amino, carboxyl, aldehyde group and the like, can greatly broaden the range of applications of polyethylene glycol, making it has a broad application prospect in organic synthesis, peptide synthesis, polymer synthesis and sustained release or controlled release of drugs, targeting administration, etc.

Polyethylene glycol active derivative has been reported in many document.

Patent document U.S. Pat. No. 5,672,662 describes the preparation of linear polyethylene glycols having an end group of propionic acid and butyric acid, and the n-hydroxy succinimide ester thereof.

Patent document U.S. Pat. No. 5,643,575 describes a u-shaped structure polyethylene glycol derivative.

Non-patent document "synthesis and curing of terminal alkyne groups polyethylene glycol" (Chinese Journal of Explosives & Propellants, December 2010, vol 33, no. 6) describes a synthesis method of alkynyl-terminated polyethylene glycol, including polyethylene glycol 400 and propyne bromine as raw materials, tetrahydrofuran as solvent, reaction in the presence of catalyst potassium tert-butoxide to obtain the product, however, the prepared polymer is a linear polyethylene glycol, it can be introduced two terminal alkyne groups at most, and can not be introduced into the other active groups.

Patent document WO 2011075953 A1 describes a novel multi-arm polyethylene glycol having different type of active groups, which formed by the polymerization of ethylene oxide, and an oligomeric pentaerythritol as the initiator. The active end group is selected from the group consisting of hydroxyl, amino, sulfhydryl, carboxyl, ester group, aldehyde group, acrylic and maleic imide group, it does not disclose active end group may be alkynyl.

To overcome the deficiencies of the prior art, the present invention provides an alkynyl multi-arm polyethylene glycol active derivative and a preparation method thereof.

SUMMARY OF THE INVENTION

One objective of the present invention is to provide an alkynyl multi-arm polyethylene glycol active derivative, compared with a linear polyethylene glycol, the multi-arm polyethylene glycol has a plurality of groups, further has a plurality of introduction points of functional groups, may load a plurality of different active end groups, solve the problems of a poor flexibility-of-use and a smaller application-scoped of alkynyl polyethylene glycol derivative.

Another object of the present invention is to provide a multi-arm polyethylene glycol-alkynyl active derivative, which can be reacted with other types of polymer, used for the preparation of gel, enabled lower reaction conditions and shorten the gel formation time.

Another object of the present invention is to provide a series of different structures of multi-arm polyethylene glycol-alkynyl active derivatives, solve the problems that the active ingredient release speed can not control when a multi-arm polyethylene glycol-alkynyl active derivative forming a gel.

One aspect of the present invention provides an alkynyl multi-arm polyethylene glycol active derivative, the multi-arm polyethylene glycol derivative having a structure of a general formula I:

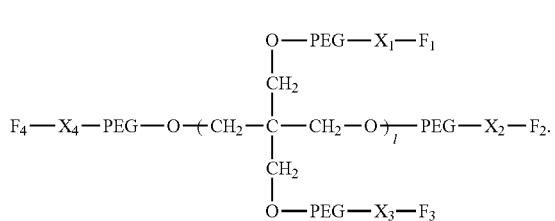

I

Another aspect of the present invention provides an alkynyl multi-arm polyethylene glycol derivative, the multi-arm polyethylene glycol derivative having a structure of a general formula X VIII:

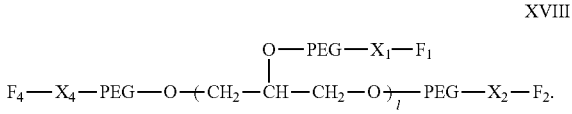

XVIII

Wherein:

PEG is the same or different $-(CH_2CH_2O)_m-$, m is an integer of average value of 3-250;

l is an integer $\geq 1$;

$X_1$, $X_2$, $X_3$ and $X_4$ are linking groups which may be the same or different, are independently selected from the group consisting of $C_{1-12}$ alkyl, aryl alkyl, ester group, carbonate group, amide group, amide ester group, ether group, and urethane group; $F_1$, $F_2$, $F_3$ and $F_4$ are end groups which may be the same or different, are independently selected from the group consisting of the following groups:

—$NH_2$, —COOH, —$OCH_3$,

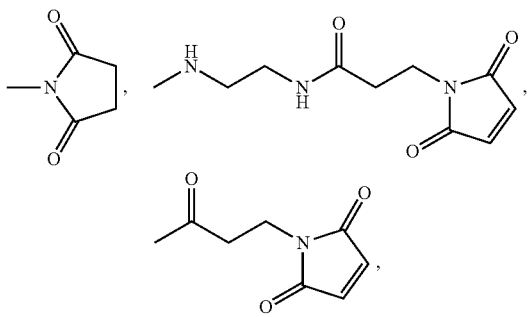

and —C≡CH. And at least one of the $F_1$, $F_2$, $F_3$ and $F_4$ is —C≡CH.

In the present invention, in the alkynyl multi-arm polyethylene glycol derivative of general formula I or general formula X VIII, preferably, an average value of m is an integer of 18-150, and more preferably, an average value of m is an integer of 18-75. In the present invention, in the alkynyl multi-arm polyethylene glycol derivative of general formula I or general formula X VIII, preferably, l is an integer ≥1 and ≤10, more preferably, l is an integer ≥1 and ≤6, most preferably, l is an integer ≥1 and ≤4, and in one embodiment of the present invention, l may be preferably 1, 2, 3, 4, 5 or 6.

In the present invention, in the alkynyl multi-arm polyethylene glycol derivative of general formula I or general formula X VIII, $X_1$, $X_2$, $X_3$ and $X_4$ are linking groups, more preferably, $X_1$, $X_2$, $X_3$ and $X_4$ are independently selected from the group consisting of —$(CH_2)_i$—, —$(CH_2)_i$NHCO$(CH_2)_j$—, —$(CH_2)_i$CONH$(CH_2)_j$—, —$(CH_2)_i$NH—, —$(CH_2)_i$OCOO—, —$(CH_2)_i$OCONH—, —$(CH_2)_i$NHCOO—, —$(CH_2)_i$NHCONH—, —OC$(CH_2)_i$COO—, —$(CH_2)_i$COO—, —$(CH_2)_i$CONH—, —$(CH_2)_i$COO—; most preferably, $X_1$, $X_2$, $X_3$ and $X_4$ are independently selected from the group consisting of —$(CH_2)_i$—, —$(CH_2)_i$NHCO$(CH_2)_j$—, —$(CH_2)_i$CONH$(CH_2)_j$—.

In the present invention, in the alkynyl multi-arm polyethylene glycol derivative of general formula I or general formula X VIII, i is an integer of 1-10 in $X_1$, $X_2$, $X_3$ and $X_4$, preferably, i is an integer of 1-5, more preferably, i is an integer of 1-3, in one present embodiment of the present invention, i is 1, 2, 3, 4 or 5.

In the present invention, in the alkynyl multi-arm polyethylene glycol derivative of general formula I or general formula X VIII, j is an integer of 1-10 in $X_1$, $X_2$, $X_3$ and $X_4$, preferably, j is an integer of 1-5, more preferably, j is an integer of 1-3, in one present embodiment of the present invention, j is 1, 2, 3, 4 or 5.

In the present invention, in the alkynyl multi-arm polyethylene glycol derivative of general formula I, at least two of the $F_1$, $F_2$, $F_3$ and $F_4$ are —C≡CH; In another embodiment of the present invention, at least three of the $F_1$, $F_2$, $F_3$ and $F_4$ are —C≡CH; In another embodiment of the present invention, $F_1$, $F_2$, $F_3$ and $F_4$ are all —C≡CH.

In the present invention, in the alkynyl multi-arm polyethylene glycol derivative of general formula X VII, at least two of the $F_1$, $F_2$ and $F_4$ are —C≡CH; In another embodiment of the present invention, $F_1$, $F_2$, $F_4$ are all —C≡CH.

In the present invention, in the alkynyl multi-arm polyethylene glycol derivative of general formula I or general formula X VIII, the multi-arm polyethylene glycol derivative has a molecular weight of 1,000-80,000 Da, in a preferred embodiment of the present invention, the multi-arm polyethylene glycol has a molecular weight of 3,000-20,000 Da, in a more preferred embodiment, the multi-arm polyethylene glycol has a molecular weight of 3,000 to about 10,000 Da, in a most preferred embodiment, the multi-arm polyethylene glycol may have a molecular weight of 3,000 Da, 5,000 Da, 10,000 Da, 20,000 Da.

In one embodiment, the multi-arm polyethylene glycol derivative is a multi-arm polyethylene glycol-alkynyl derivative having a structure of a general formula II:

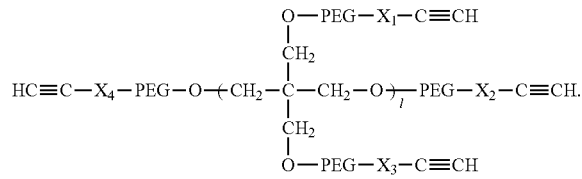

II

In one embodiment, in the multi-arm polyethylene glycol-alkynyl derivative having a general formula II, $X_1$, $X_2$, $X_3$ and $X_4$ are independently selected from the group consisting of —$(CH_2)_i$—, —$(CH_2)_i$NHCO$(CH_2)_j$—, —$(CH_2)_i$CONH$(CH_2)_j$—; i is an integer of 1-10, preferably, i is an integer of 1-5, more preferably, i is 1, 2, 3, 4 or 5; j is an integer of 1-10, preferably, j is an integer of 1-5, more preferably, j is 1, 2, 3, 4 or 5.

In one embodiment, the multi-arm polyethylene glycol derivative is a multi-arm polyethylene glycol mono-alkynyl multi-acid derivative having a structure of a general formula III:

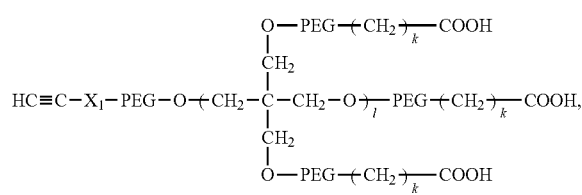

III

Wherein, the PEG, l and $X_1$ are same as defined in general formula I or general formula III, k is an integer of 1-10.

In one embodiment, in the multi-arm polyethylene glycol mono-alkynyl multi-acid derivative having a structure of a general formula III, preferably, wherein $X_1$ is —$(CH_2)_i$— or —$(CH_2)_i$NHCO$(CH_2)_j$—; i is an integer of 1-10, preferably, i is an integer of 1-5, more preferably, i is 1, 2, 3, 4 or 5; j is an integer of 1-10, preferably, j is an integer of 1-5, more preferably, j is 1, 2, 3, 4 or 5; k is an integer of 1-10, preferably, k is an integer of 1-5, more preferably, k is 1, 2, 3, 4 or 5.

In one embodiment, the multi-arm polyethylene glycol derivative is a multi-arm polyethylene glycol multi-alkynyl multi-acid derivative having a structure of a general formula IV:

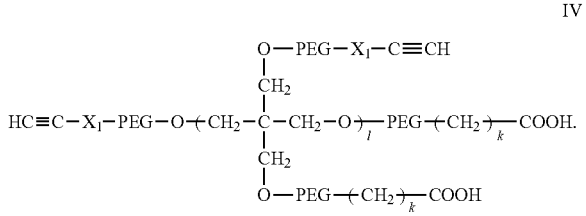

Wherein, the PEG, 1 and $X_1$ are same as defined in general formula I or general formula V III, k is an integer of 1-10.

In one embodiment, in the multi-arm polyethylene glycol multi-alkynyl multi-acid derivative having a structure of a general formula IV, preferably, wherein $X_1$ is —$(CH_2)_i$— or —$(CH_2)_i NHCO(CH_2)_j$—; i is an integer of 1-10, preferably, i is an integer of 1-5, more preferably, i is 1, 2, 3, 4 or 5; j is an integer of 1-10, preferably, j is an integer of 1-5, more preferably, j is 1, 2, 3, 4 or 5; k is an integer of 1-10, preferably, k is an integer of 1-5, more preferably, k is 1, 2, 3, 4 or 5.

In one embodiment, the multi-arm polyethylene glycol derivative is a multi-arm polyethylene glycol multi-alkynyl mono-acid derivative having a structure of a general formula V:

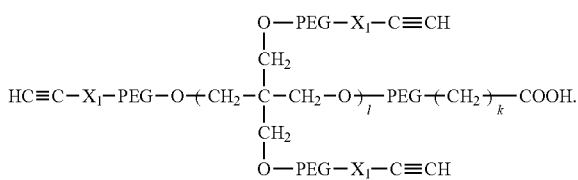

Wherein, the PEG, 1 and $X_1$ are same as defined in general formula I or general formula V III, k is an integer of 1-10.

In one embodiment, in the multi-arm polyethylene glycol multi-alkynyl mono-acid derivative having a structure of a general formula V, preferably, wherein $X_1$ is —$(CH_2)_i$— or —$(CH_2)_i NHCO(CH_2)_j$—; i is an integer of 1-10, preferably, i is an integer of 1-5, more preferably, i is 1, 2, 3, 4 or 5; j is an integer of 1-10, preferably, j is an integer of 1-5, more preferably, j is 1, 2, 3, 4 or 5; k is an integer of 1-10, preferably, k is an integer of 1-5, more preferably, k is 1, 2, 3, 4 or 5.

In one embodiment, the multi-arm polyethylene glycol derivative is a multi-arm polyethylene glycol mono-alkynyl multi-acid active NHS ester derivative having a structure of a general formula VI:

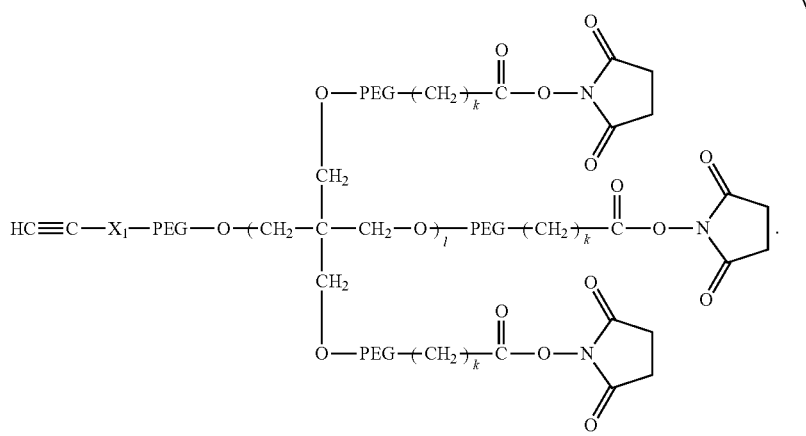

Wherein, the PEG, 1 and $X_1$ are same as defined in general formula I or general formula V III, k is an integer of 1-10.

In one embodiment, in the multi-arm polyethylene glycol mono-alkynyl multi-acid active NHS ester derivative having a structure of a general formula VI, preferably, wherein $X_1$ is —$(CH_2)_i$— or —$(CH_2)_i NHCO(CH_2)_j$—; i is an integer of 1-10, preferably, i is an integer of 1-5, more preferably, i is 1, 2, 3, 4 or 5; j is an integer of 1-10, preferably, j is an integer of 1-5, more preferably, j is 1, 2, 3, 4 or 5; k is an integer of 1-10, preferably, k is an integer of 1-5, more preferably, k is 1, 2, 3, 4 or 5.

In one embodiment, the multi-arm polyethylene glycol derivative is a multi-arm polyethylene glycol multi-alkynyl multi-acid active NHS ester derivative having a structure of a general formula VII:

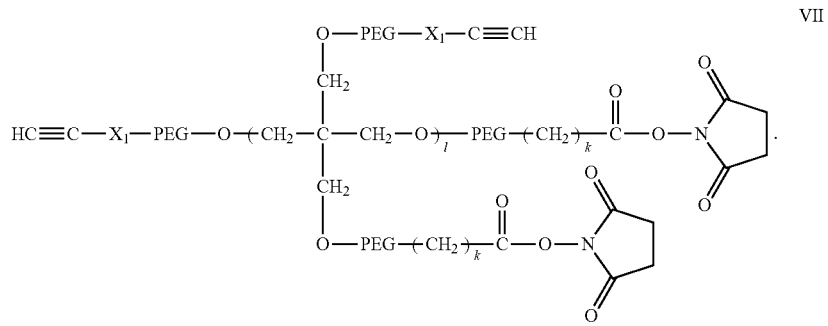

VII

Wherein, the PEG, 1 and $X_1$ are same as defined in general formula I or general formula V III, k is an integer of 1-10.

In one embodiment, in the multi-arm polyethylene glycol multi-alkynyl multi-acid active NHS ester derivative having a structure of a general formula VII, preferably, wherein $X_1$ is —$(CH_2)_i$— or —$(CH_2)_i NHCO(CH_2)_j$—; i is an integer of 1-10, preferably, i is an integer of 1-5, more preferably, i is 1, 2, 3, 4 or 5; j is an integer of 1-10, preferably, j is an integer of 1-5, more preferably, j is 1, 2, 3, 4 or 5; k is an integer of 1-10, preferably, k is an integer of 1-5, more preferably, k is 1, 2, 3, 4 or 5.

In one embodiment, the multi-arm polyethylene glycol derivative is a multi-arm polyethylene glycol multi-alkynyl mono-acid active NHS ester derivative having a structure of a general formula VI:

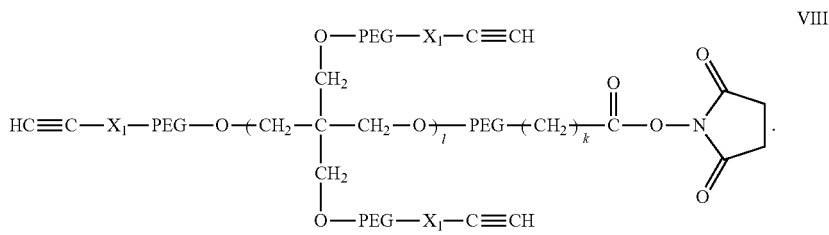

VIII

Wherein, the PEG, 1 and $X_1$ are same as defined in general formula I or general formula V III, k is an integer of 1-10.

In one embodiment, the multi-arm polyethylene glycol multi-alkynyl mono-acid active NHS ester derivative having a structure of a general formula VII, preferably, wherein $X_1$ is —$(CH_2)_i$— or —$(CH_2)_i NHCO(CH_2)_j$—; i is an integer of 1-10, preferably, i is an integer of 1-5, more preferably, i is 1, 2, 3, 4 or 5; j is an integer of 1-10, preferably, j is an integer of 1-5, more preferably, j is 1, 2, 3, 4 or 5; k is an integer of 1-10, preferably, k is an integer of 1-5, more preferably, k is 1, 2, 3, 4 or 5.

In one embodiment, the multi-arm polyethylene glycol derivative is a multi-arm polyethylene glycol mono-alkynyl multi-acid active MAL derivative having a structure of a general formula IX:

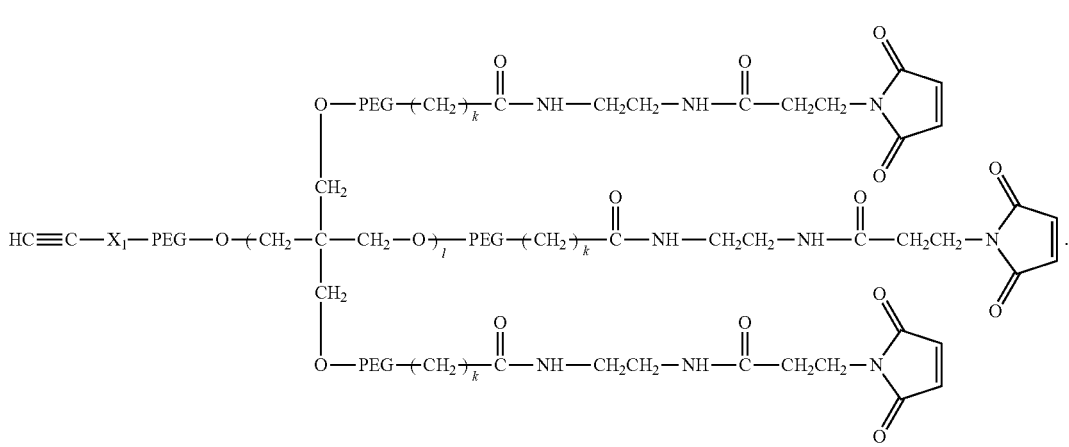

IX

Wherein, the PEG, 1 and $X_1$ are same as defined in general formula I or general formula V III, k is an integer of 1-10.

In one embodiment, in the multi-arm polyethylene glycol mono-alkynyl multi-acid active MAL derivative having a structure of a general formula IX, preferably, wherein $X_1$ is —$(CH_2)_i$— or —$(CH_2)_iNHCO(CH_2)_j$—; i is an integer of 1-10, preferably, i is an integer of 1-5, more preferably, i is 1, 2, 3, 4 or 5; j is an integer of 1-10, preferably, j is an integer of 1-5, more preferably, j is 1, 2, 3, 4 or 5; k is an integer of 1-10, preferably, k is an integer of 1-5, more preferably, k is 1, 2, 3, 4 or 5.

In one embodiment, the multi-arm polyethylene glycol derivative is a multi-arm polyethylene glycol multi-alkynyl multi-acid active MAL derivative having a structure of a general formula X:

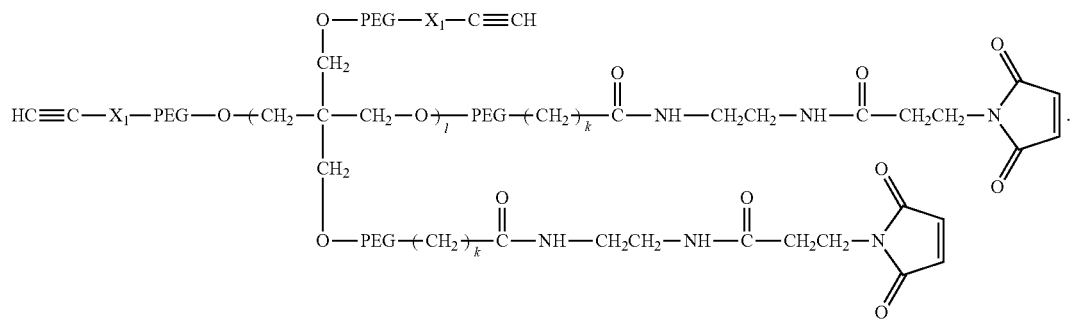

Wherein, the PEG, 1 and $X_1$ are same as defined in general formula I or general formula V III, k is an integer of 1-10.

In one embodiment, in the multi-arm polyethylene glycol multi-alkynyl multi-acid active MAL derivative having a structure of a general formula X, preferably, wherein $X_1$ is —$(CH_2)_i$— or —$(CH_2)_iNHCO(CH_2)_j$—; i is an integer of 1-10, preferably, i is an integer of 1-5, more preferably, i is 1, 2, 3, 4 or 5; j is an integer of 1-10, preferably, j is an integer of 1-5, more preferably, j is 1, 2, 3, 4 or 5; k is an integer of 1-10, preferably, k is an integer of 1-5, more preferably, k is 1, 2, 3, 4 or 5.

In one embodiment, the multi-arm polyethylene glycol derivative is a multi-arm polyethylene glycol multi-alkynyl mono-acid active MAL derivative having a structure of a general formula XI:

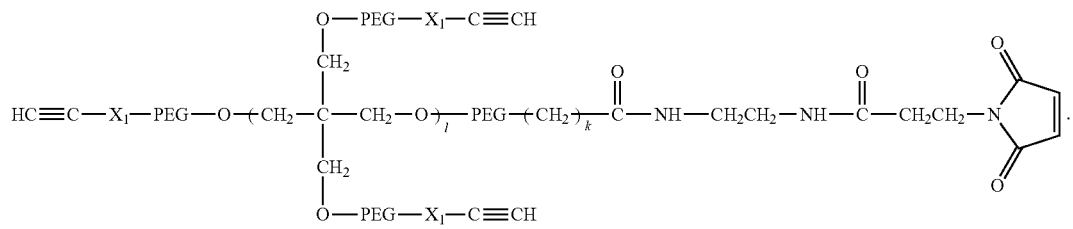

Wherein, the PEG, 1 and $X_1$ are same as defined in general formula I or general formula V III, k is an integer of 1-10.

In one embodiment, in the multi-arm polyethylene glycol multi-alkynyl mono-acid active MAL derivative having a structure of a general formula XI, preferably, wherein $X_1$ is —$(CH_2)_i$— or —$(CH_2)_iNHCO(CH_2)_j$—; i is an integer of 1-10, preferably, i is an integer of 1-5, more preferably, i is 1, 2, 3, 4 or 5; j is an integer of 1-10, preferably, j is an integer of 1-5, more preferably, j is 1, 2, 3, 4 or 5; k is an integer of 1-10, preferably, k is an integer of 1-5, more preferably, k is 1, 2, 3, 4 or 5.

In one embodiment, the multi-arm polyethylene glycol derivative is a multi-arm polyethylene glycol mono-alkynyl multi-amine derivative having a structure of a general formula XII:

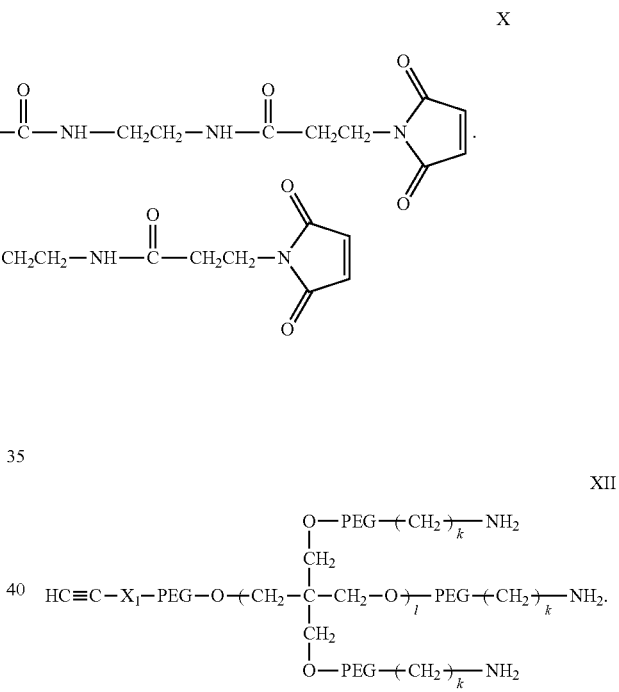

Wherein, the PEG, 1 and $X_1$ are same as defined in general formula I or general formula V III, k is an integer of 1-10.

In one embodiment, in the multi-arm polyethylene glycol mono-alkynyl multi-amine derivative having a structure of a general formula XII, preferably, wherein $X_1$ is —$(CH_2)_i$— or —$(CH_2)_iCONH(CH_2)_j$—; i is an integer of 1-10, preferably, i is an integer of 1-5, more preferably, i is 1, 2, 3, 4 or 5; j is an integer of 1-10, preferably, j is an integer of 1-5, more preferably, j is 1, 2, 3, 4 or 5; k is an integer of 1-10, preferably, k is an integer of 1-5, more preferably, k is 1, 2, 3, 4 or 5.

In one embodiment, the multi-arm polyethylene glycol derivative is a multi-arm polyethylene glycol multi-alkynyl multi-amine derivative having a structure of a general formula X III:

XIII

HC≡C—X₁—PEG—O—(CH₂—C(—CH₂—O)ₗ—PEG—(CH₂)ₖ—NH₂)(CH₂—O—PEG—X₁—C≡CH)(CH₂—O—PEG—X₁—C≡CH)(O—PEG—(CH₂)ₖ—NH₂)

Wherein, the PEG, 1 and $X_1$ are same as defined in general formula I or general formula V III, k is an integer of 1-10.

In one embodiment, in the multi-arm polyethylene glycol multi-alkynyl multi-amine derivative having a structure of a general formula X III, preferably, wherein $X_1$ is —(CH$_2$)$_i$— or —(CH$_2$)$_i$CONH(CH$_2$)$_j$—; i is an integer of 1-10, preferably, i is an integer of 1-5, more preferably, i is 1, 2, 3, 4 or 5; j is an integer of 1-10, preferably, j is an integer of 1-5, more preferably, j is 1, 2, 3, 4 or 5; k is an integer of 1-10, preferably, k is an integer of 1-5, more preferably, k is 1, 2, 3, 4 or 5.

In one embodiment, the multi-arm polyethylene glycol derivative is a multi-arm polyethylene glycol multi-alkynyl mono-amine derivative having a structure of a general formula X IV:

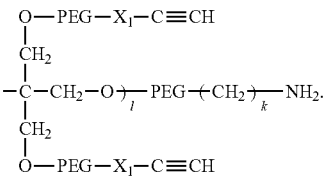

Wherein, the PEG, 1 and $X_1$ are same as defined in general formula I or general formula V III, k is an integer of 1-10.

In one embodiment, in the multi-arm polyethylene glycol multi-alkynyl mono-amine derivative having a structure of a general formula X IV, preferably, wherein $X_1$ is —(CH$_2$)$_i$— or —(CH$_2$)$_i$CONH(CH$_2$)$_j$—; i is an integer of 1-10, preferably, i is an integer of 1-5, more preferably, i is 1, 2, 3, 4 or 5; j is an integer of 1-10, preferably, j is an integer of 1-5, more preferably, j is 1, 2, 3, 4 or 5; k is an integer of 1-10, preferably, k is an integer of 1-5, more preferably, k is 1, 2, 3, 4 or 5.

In one embodiment, the multi-arm polyethylene glycol derivative is a multi-arm polyethylene glycol mono-alkynyl multi-amine active MAL derivative having a structure of a general formula X V:

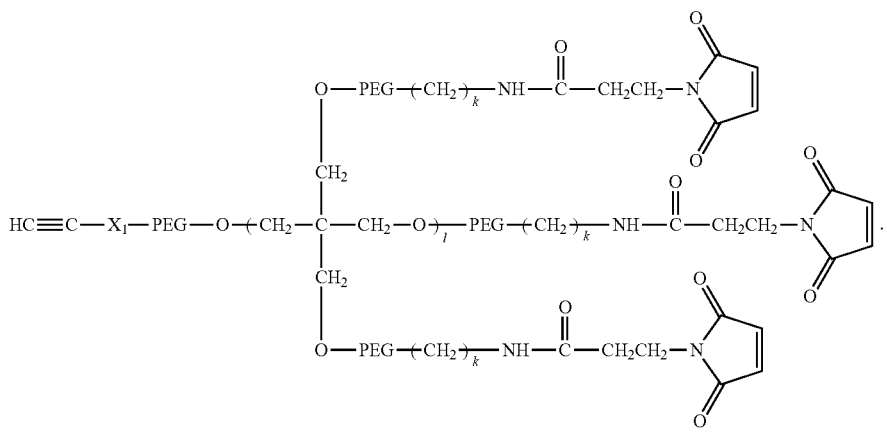

Wherein, the PEG, 1 and $X_1$ are same as defined in general formula I or general formula V III, k is an integer of 1-10.

In one embodiment, in the multi-arm polyethylene glycol mono-alkynyl multi-amine active MAL derivative having a structure of a general formula X V, preferably, wherein $X_1$ is —(CH$_2$)$_i$— or —(CH$_2$)$_i$CONH(CH$_2$)$_j$—; i is an integer of 1-10, preferably, i is an integer of 1-5, more preferably, i is 1, 2, 3, 4 or 5; j is an integer of 1-10, preferably, j is an integer of 1-5, more preferably, j is 1, 2, 3, 4 or 5; k is an integer of 1-10, preferably, k is an integer of 1-5, more preferably, k is 1, 2, 3, 4 or 5.

In one embodiment, the multi-arm polyethylene glycol derivative is a multi-arm polyethylene glycol multi-alkynyl multi-amine active MAL derivative having a structure of a general formula X VI:

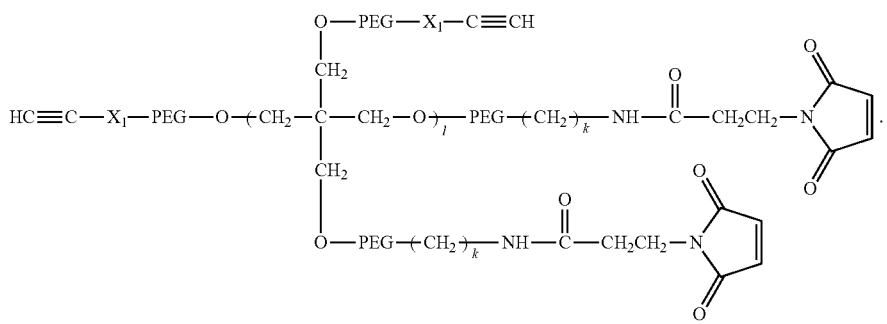

XVI

Wherein, the PEG, 1 and $X_1$ are same as defined in general formula I or general formula V III, k is an integer of 1-10.

In one embodiment, in the multi-arm polyethylene glycol multi-alkynyl multi-amine active MAL derivative having a structure of a general formula X VI, preferably, wherein $X_1$ is —$(CH_2)_i$— or —$(CH_2)_i CONH(CH_2)_j$—; i is an integer of 1-10, preferably, i is an integer of 1-5, more preferably, i is 1, 2, 3, 4 or 5; j is an integer of 1-10, preferably, j is an integer of 1-5, more preferably, j is 1, 2, 3, 4 or 5; k is an integer of 1-10, preferably, k is an integer of 1-5, more preferably, k is 1, 2, 3, 4 or 5.

In one embodiment, the multi-arm polyethylene glycol derivative is a multi-arm polyethylene glycol multi-alkynyl mono-amine active MAL derivative having a structure of a general formula X VII:

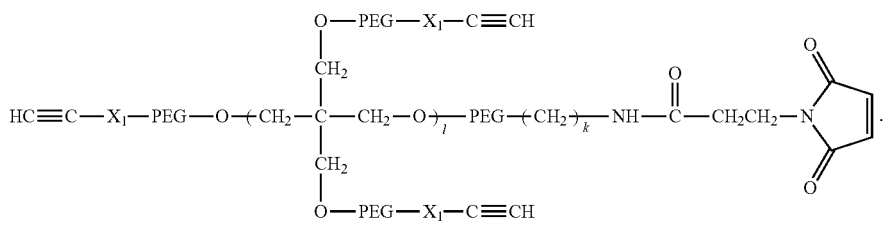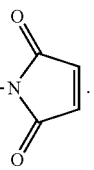

XVII

Wherein, the PEG, 1 and $X_1$ are same as defined in general formula I or general formula V III, k is an integer of 1-10.

In one embodiment, in the multi-arm polyethylene glycol multi-alkynyl mono-amine active MAL derivative having a structure of a general formula X VII, preferably, wherein $X_1$ is —$(CH_2)_i$— or —$(CH_2)_i CONH(CH_2)_j$—; i is an integer of 1-10, preferably, i is an integer of 1-5, more preferably, i is 1, 2, 3, 4 or 5; j is an integer of 1-10, preferably, j is an integer of 1-5, more preferably, j is 1, 2, 3, 4 or 5; k is an integer of 1-10, preferably, k is an integer of 1-5, more preferably, k is 1, 2, 3, 4 or 5.

Another aspect of the present invention further provides a method for preparing an alkynyl multi-arm polyethylene glycol derivative, comprising: dissolving a multi-arm polyethylene glycol in a solvent, adding sodium hydride and reaction at room temperature, adding propargyl bromide and potassium iodide and reaction, obtaining a multi-arm polyethylene glycol-propynyl after separation.

Another aspect of the present invention further provides a method for preparing an alkynyl multi-arm polyethylene glycol derivative, comprising: dissolving a multi-arm polyethylene glycol-to-end acetic acid and N-hydroxy succinimide (NHS) in a solvent, adding N,N'-dicyclohexyl-carbodiimide (DCC) and reaction, adding propargyl amine and reaction, obtaining a multi-arm polyethylene glycol-propynyl acetamide after separation.

Another aspect of the present invention further provides a method for preparing an alkynyl multi-arm polyethylene glycol derivative, comprising: dissolving a multi-arm polyethylene glycol-to-end hydroxyl-to-end acetic acid methyl ester in a solvent, adding sodium hydride and reaction at room temperature, adding propargyl bromide and potassium iodide and reaction, obtaining a multi-arm polyethylene glycol-propynyl-acetic acid methyl ester; hydrolyzing the multi-arm polyethylene glycol-propynyl-acetic acid methyl ester, obtaining a polyethylene glycol-propynyl-acetic acid derivative.

Further, another aspect of the present invention also provides a method for preparing an alkynyl multi-arm polyethylene glycol derivative, comprising: dissolving a multi-arm polyethylene glycol-to-end hydroxyl-to-end acetic acid methyl ester in a solvent, adding sodium hydride and reaction at room temperature, adding propargyl bromide and potassium iodide and reaction, obtaining a multi-arm polyethylene glycol-propynyl-acetic acid methyl ester; hydrolyzing the multi-arm polyethylene glycol-propynyl-acetic acid methyl ester, obtaining a polyethylene glycol-propynyl-acetic acid derivative; dissolving the polyethylene glycol-propynyl-acetic acid derivative in a solvent, adding N-hydroxy succinimide (NHS) and N,N'-dicyclohexyl-carbodiimide (DCC) and reaction, obtaining a multi-arm polyethylene glycol-propynyl-acetic acid NHS ester.

Further, another aspect of the present invention also provides a method for preparing an alkynyl multi-arm polyethylene glycol derivative, comprising: dissolving a multi-arm polyethylene glycol-to-end hydroxyl-to-end acetic acid methyl ester in a solvent, adding sodium hydride and reaction at room temperature, adding propargyl bromide and potassium iodide and reaction, obtaining a multi-arm polyethylene glycol-propynyl-acetic acid methyl ester; hydrolyzing the multi-arm polyethylene glycol-propynyl-acetic acid methyl ester, obtaining a polyethylene glycol-propynyl-acetic acid derivative; dissolving the polyethylene glycol-propynyl-acetic acid derivative in a solvent, adding N-hydroxy succinimide (NHS) and N,N'-dicyclohexyl-carbodiimide (DCC) and reaction, adding maleimido-ethylene-diamine and reaction, obtaining a multi-arm polyethylene glycol-to-end propynyl-to-end acetic acid MAL ester.

Another aspect of the present invention further provides a method for preparing an alkynyl multi-arm polyethylene glycol derivative, comprising: dissolving a multi-arm polyethylene glycol-to-end acetic acid-to-end ethyl amine in a solvent, adding triethylamine and di-tert-butyl dicarbonate (Boc$_2$O) and reaction, obtaining a multi-arm polyethylene glycol-acetic acid-Boc amide; after the reaction, dissolving the multi-arm polyethylene glycol-acetic acid-Boc amide and 0.086 g of N-hydroxy succinimide (NHS) in a solvent, adding N,N'-dicyclohexyl-carbodiimide (DCC) and reaction, adding propargyl amine and reaction, obtaining a multi-arm polyethylene glycol-alkynyl-Boc amide; dissolving the multi-arm polyethylene glycol-alkynyl-Boc amide in a solvent, adding trifluoro acetic acid and reaction, obtaining a multi-arm polyethylene glycol-to-end alkynyl-to-end ethyl amine.

Further, another aspect of the present invention also provides a method for preparing an alkynyl multi-arm polyethylene glycol derivative, comprising: dissolving a multi-arm polyethylene glycol-to-end acetic acid-to-end ethyl amine in a solvent, adding triethylamine and di-tert-butyl dicarbonate (Boc$_2$O) and reaction, obtaining a multi-arm polyethylene glycol-acetic acid-Boc amide; after the reaction, dissolving the multi-arm polyethylene glycol-acetic acid-Boc amide and N-hydroxy succinimide (NHS) in a solvent, adding N,N'-dicyclohexyl-carbodiimide (DCC) and reaction, adding propargyl amine and reaction, obtaining a multi-arm polyethylene glycol-alkynyl-Boc amide; dissolving the multi-arm polyethylene glycol-alkynyl-Boc amide in a solvent, adding trifluoro acetic acid and reaction, obtaining a multi-arm polyethylene glycol-to-end alkynyl-to-end ethyl amine; dissolving the multi-arm polyethylene glycol-to-end alkynyl-to-end ethyl amine in a solvent, adding 3-maleimidopropionic acid N-hydroxysuccinimide ester and reaction, obtaining a multi-arm polyethylene glycol-to-end alkynyl-to-end ethyl amine MAL.

In the method for preparing an alkynyl multi-arm polyethylene glycol derivative of the present invention, the multi-arm polyethylene glycol, the multi-arm polyethylene glycol-to-end acetic acid, the multi-arm polyethylene glycol-to-end hydroxyl-to-end acetic acid methyl ester, the multi-arm polyethylene glycol-to-end acetic acid-to-end ethyl amine may be commercially available, or prepared by the method in patent CN102108119A.

In the method for preparing an alkynyl multi-arm polyethylene glycol derivative of the present invention, the solvent may be the suitable solvent well-known in the art, selected from the group consisting of methanol, ethanol, chloroform, methylene chloride, acetone, diethyl ether, ethyl acetate, and the like.

The alkynyl multi-arm polyethylene glycol derivative of the present invention may be used to conjugated with protein, peptide or drug active small molecule, may increase the targeting ability and drug efficacy, reduce the toxicity. The protein, peptide or drug active small molecule include, but are not limited to, analgesics and anti-inflammatory agents, antacids, anthelmintics, anti-arrhythmia agents, anti-bacterial agents, anticoagulants, anti-depressants, antidiabetic agents, antidiarrheal agents, anti-epileptic agents, anti-fungal agents, anti-gout agents, anti-hypertensive drugs, anti-malarials, anti-migraine agents, anti-muscarinic agents, anti-tumor agents and immunosuppressive agents, anti-protozoal agents, anti-rheumatic agents, anti-thyroid agents, anti-viral agents, anti-anxiety agents, sedative agents, ophthalmic drugs and tranquilizers, β-receptor blocking agents, cardiac-contraction agents, corticosteroids, cough suppressants, cytotoxic agents, decongestants, diuretics, enzymes, anti-parkinsonian agents, gastrointestinal agents, histamine receptor antagonists, grease modulating agents, local anesthetics, neuromuscular blocking agents, nitrate and anti-anginal agents, nutritional agents, narcotic analgesics, oral vaccines, proteins, peptides and recombinant drugs, sex hormones and contraceptives, spermicidal agents, and stimulants (immunostimulating agents).

The method of conjugating the alkynyl multi-arm polyethylene glycol derivative of the present invention with protein, peptide or drug active small molecule, may be as described in patent document CN102108119A, conjugates formed via combination end groups with drug molecules, preferably via combination —COOH or

with protein, peptide or drug active small molecule.

Compared with the linear polyethylene glycol, the alkynyl multi-arm polyethylene glycol derivative has a plurality of branches, further has a plurality of introduction points of functional groups, may load a plurality of active end groups.

At the same time, the alkynyl multi-arm polyethylene glycol derivative of the present invention may improve the load rate of the alkynyl active end groups significantly, it is also possible to load other different active end groups, hence the multi-arm polyethylene glycol derivative has a greater flexibility and a more wide range of applications, and has a good application prospect in organic synthesis, drug synthesis and medical apparatus, etc.

In addition, the alkynyl multi-arm polyethylene glycol derivative of the present invention may be reacted with another polymer, in particular reacted with polyethylene glycol azido derivative, to form gel. The release rate of the active ingredient may be controlled by changing the molecular weight or the number of branches of the alkynyl multi-arm polyethylene glycol derivative.

DETAILED DESCRIPTION OF THE INVENTION

Examples below describes the derivatives and the preparation method thereof of the present invention, the examples are not intended to limit the invention, the scope of the invention is limited by the claims of the application.

Example 1

Preparation of Four-Arm Polyethylene Glycol (10,000 Da)-Propynyl

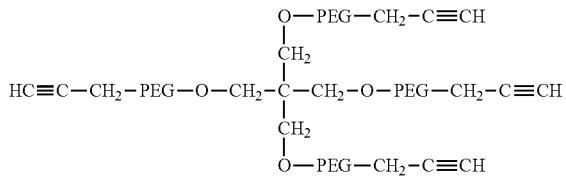

10.0 g of a four-arm polyethylene glycol (10,000 Da) was dissolved in 150 mL of tetrahydrofuran, lowered the temperature to 0° C. under nitrogen, 0.48 g of sodium hydride was added, reacted at room temperature for 0.5 hours, 22.4 mL of propargyl bromide (80% solution in toluene) was added, 0.09 g of potassium iodide was added, heated to reflux for 2 hours protected from light, cooled, 100 mL of water was added, out of the tetrahydrofuran, extracted with methylene chloride for three times, dried with anhydrous sodium sulfate, filtered, and concentrated to a viscous at 45° C., precipitated with 100 mL of ethyl ether, the precipitate was collected by filtration and dried under vacuum. The resulting 8.7 g of four-arm polyethylene glycol-propynyl.

1H-NMR (DMSO) δ: 3.08 (s, —C≡CH, 4H)

Example 2

Preparation of Eight-Arm Polyethylene Glycol (20,000 Da)-Propynyl Acetamide

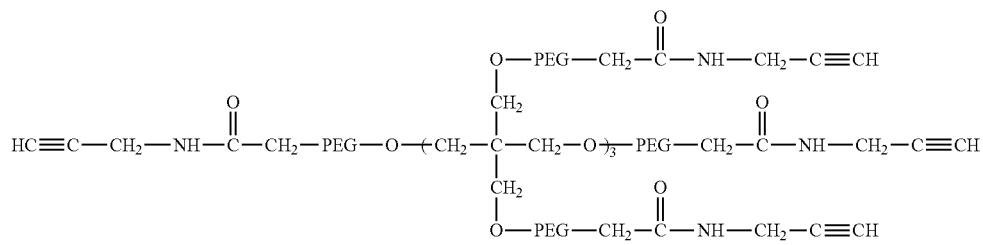

10.0 g of a eight-arm polyethylene glycol (20,000 Da)-acetic acid and 0.69 g of N-hydroxy succinimide (NHS) was dissolved in 100 mL of methylene chloride under nitrogen, 1.32 g of N,N'-dicyclohexyl-carbodiimide (DCC) was added, reaction for 4 h, 0.9 mL of propargyl amine was added, the reaction was allowed to proceed overnight protected from light, filtered, concentrated at 40° C., 150 mL of isopropyl alcohol was heated to dissolve and precipitated with an ice-water bath, filtered, washed the filter cake with isopropanol twice, dried under vacuum. The resulting 9.0 g of eight-arm polyethylene glycol-propynyl acetamide.

1H-NMR (DMSO) δ: 3.08 (s, —C≡CH, 4H), 7.66 (t, CONH, 4H)

Example 3

Preparation of Four-Arm Polyethylene Glycol (5,000 Da)-Alkynyl- to Mono-Acetic Acid

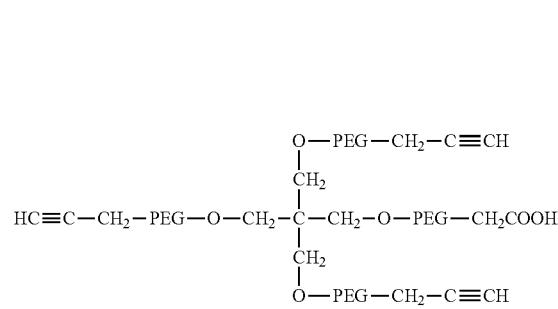

10.0 g of a four-arm polyethylene glycol (5,000 Da)-hydroxy-mono-acetic acid methyl ester was dissolved in 150 mL of tetrahydrofuran, lowered the temperature to 0° C. under nitrogen atmosphere, 0.72 g of sodium hydride was added, reacted at room temperature for 0.5 hours, 33.6 mL of propargyl bromide (80% solution in toluene) was added, 0.135 g of potassium iodide was added, heated to reflux for 2 hours protected from light, cooled, 100 mL of water was added, out of the tetrahydrofuran, extracted with methylene chloride for three times, dried with anhydrous sodium sulfate, filtered, and concentrated to a viscous at 45° C., 100 mL of ethyl ether was added for precipitation, the precipitate was collected by filtration and dried under vacuum. The resulting 8.2 g of four-arm polyethylene glycol-propynyl mono-acetic acid methyl ester.

5.0 g of a four-arm polyethylene glycol-propynyl mono-acetic acid methyl ester was dissolved in 50 mL of degassed water, 0.5 N aqueous sodium hydroxide to mediate pH 12.0, reacted at room temperature for 2-2.5 hours, 1 N aqueous hydrochloric acid to mediate pH 2-3, 6.0 g of sodium chloride was added, extracted with 50 mL of methylene chloride for three times, combined organic phase, dried with anhydrous sodium sulfate, filtered, concentrated to a viscous at 45° C., 75 mL of ethyl ether was added for precipitation, the precipitate was collected by filtration and dried under vacuum. The resulting 3.6 g of four-arm polyethylene glycol-propynyl-mono acetic acid.

1H-NMR (DMSO) δ: 3.08 (s, —C≡CH, 4H), 4.01 (s, CH2COOH, 8H)

Example 4

Preparation of Four-Arm Polyethylene Glycol (5,000 Da)-Alkynyl-Mono Acetic Acid Active NHS Ester

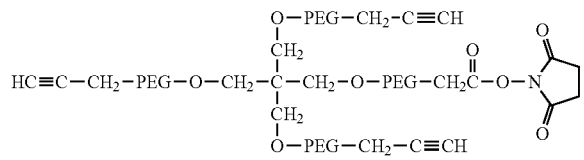

Weighed 1.0 g of four-arm polyethylene glycol (5,000 Da)-propynyl mono-acetic acid and 0.0276 g of N-hydroxy succinimide (NHS), dissolved with 10 mL of methylene chloride, under nitrogen, 0.0536 g of N,N'-dicyclohexyl-carbodiimide (DCC) was added, a sealed reaction overnight, filtered, concentrated to dryness at 40° C., 20 mL of isopropanol was heated to dissolve and precipitated with an ice-water bath, filtered, washed the filter cake with isopropanol twice, dried under the vacuum to obtain the four-arm polyethylene glycol-propynyl-mono-acetic acid NHS ester.

1H-NMR (DMSO) δ: 3.08 (s, —C≡CH, 3H), 4.6 (s, CH$_2$CO, 2H), 2.8 (s, CH$_2$ ring, 4H)

Example 5

Preparation of Four-Arm Polyethylene Glycol (5,000 Da)-Alkynyl Mono-Acetic Acid MAL

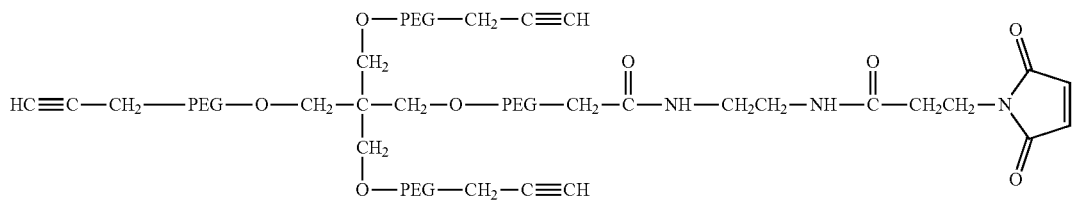

Weighed 1.0 g of four-arm polyethylene glycol (5,000 Da)-propynyl-mono-acetic acid and 0.035 g of n-hydroxy succinimide (NHS), dissolved with 10 mL of methylene chloride, under nitrogen atmosphere, 0.066 g of N,N'-dicyclohexyl-carbodiimide (DCC) was added and dissolved with 10 mL of methylene chloride, reaction for 4 h, 0.115 g of maleic anhydride ethylene-amine was added, the reaction was allowed to proceed overnight protected from light, concentrated to dryness at 40° C., 20 mL of isopropanol was heated to dissolve and precipitated with an ice-water bath, filtered, washed the filter cake with isopropanol twice, dried under the vacuum to obtain the four-arm polyethylene glycol-propynyl-mono-acetic acid MAL.

1H-NMR (DMSO) δ: 3.08 (s, —C≡CH, 3H), 2.32 (t, CH$_2$N, 2H), 7.0 (s, CH ring, 2H)

Example 6

Preparation of Four-Arm Polyethylene Glycol (20,000 Da)-Dialkynyl-Diethylamine

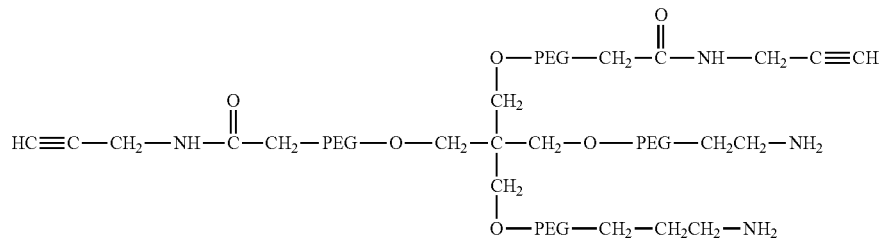

10.0 g of four-arm polyethylene glycol-diacetic acid-diethylamine (molecular weight of 20,000) was dissolved in 100 mL of methylene chloride, 0.15 mL of triethylamine was added, stirred for 10 minutes, 0.3 mL of di-tert-butyl dicarbonate (Boc$_2$O) was added, reacted at room temperature overnight, concentrated at 45° C., precipitated with 100 mL of diethyl ether, filtered, dried under the vacuum to obtain 9.7 g of four-arm polyethylene glycol-di-acetic acid-di-Boc amide.

5 g of four-arm polyethylene glycol-diacetic acid-di-Boc amide and 0.086 g of N-hydroxy succinimide (NHS) were dissolved in 50 mL of methylene chloride, under nitrogen atmosphere, 0.165 g of N,N'-dicyclohexyl-carbodiimide (DCC) was added, reaction for 4 h, 0.11 mL of propargyl amine was added, a sealed reaction overnight and filtered, concentrated to dryness at 40° C., 75 mL of isopropanol was heated to dissolve and precipitated with an ice-water bath, filtered, washed the filter cake with isopropanol twice, dried under the vacuum to obtain 4.3 g of four-arm polyethylene glycol-di alkynyl-di-BOC amide.

3.0 g of four-arm polyethylene glycol-di-alkynyl-di-BOC amide was dissolved in 21 mL of methylene chloride, 9 mL of trifluoroacetic acid was added, reaction for 3 hours, concentrated at 45° C., precipitated with 60 mL of diethyl ether, filtered, dried under the vacuum to obtain 2.3 g of four-arm polyethylene glycol-di-alkynyl-diethylamine.

1H-NMR (DMSO) δ: 3.08 (s, —C≡CH, 2H), 3.0 (m, CH$_2$N, 4H)

Example 7

Preparation of Four-Arm Polyethylene Glycol (20,000 Da)-Dialkynyl-Diethylamine-MAL

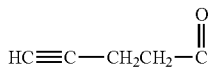

1.0 g of four-arm polyethylene glycol (20,000 Da)-di-alkynyl-diethyl amine was dissolved in 10 mL of methylene chloride, 0.035 g of 3-maleimidopropionic acid hydroxy-succinimide ester was added, the reaction was allowed to proceed overnight protected from light, concentrated to dryness at 40° C., 20 mL of isopropanol was heated to dissolve and precipitated with an ice-water bath, filtered, washed the filter cake with isopropanol twice, dried under the vacuum to obtain the four-arm polyethylene glycol-dialkynyl-diethylamine MAL.

1H-NMR (DMSO) δ: 3.08 (s, —C≡CH, 2H), 2.32 (t, CH$_2$N, 4H), 7.0 (s, CH ring, 4H)

Example 8

Preparation of Eight-Arm Polyethylene Glycol (10,000 Da)-Mono-Alkynyl-Seven-Acetic Acid

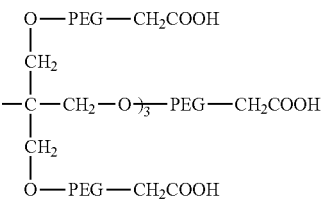

14.7 g of 4-alkynyl-acid was dissolved in 100 mL of methylene chloride, 1.89 g of N-hydroxy succinimide (NHS) was added, under nitrogen atmosphere, 3.75 g of N,N'-dicyclohexyl-carbodiimide (DCC) was added, a sealed reaction overnight at room temperature, 10 g of eight arm polyethylene glycol (10,000 Da)-mono-hydroxy-seven-acetic acid methyl ester was dissolved in 100 mL of methylene chloride, the above solution was added to the reaction flask, reaction for 4 hours, filtered, concentrated to dryness at 40° C., 20 mL of isopropanol was heated to dissolve and precipitated with an ice-water bath, filtered, washed the filter cake with isopropanol twice, dried under the vacuum to obtain 8.3 g of eight-arm polyethylene glycol-mono-alkynyl-seven-acetic acid methyl ester.

The above eight-arm polyethylene glycol-mono-alkynyl-seven acetic acid methyl ester 5.0 g was dissolved in 50 mL of degassed water, 0.5 N of aqueous sodium hydroxide to mediate pH 12.0, reacted for 2 to 2.5 hours at room temperature, 1 N aqueous hydrochloric acid to mediate pH 2-3, 6.0 g of sodium chloride was added, extracted with 50 mL of methylene chloride for three times, combined the

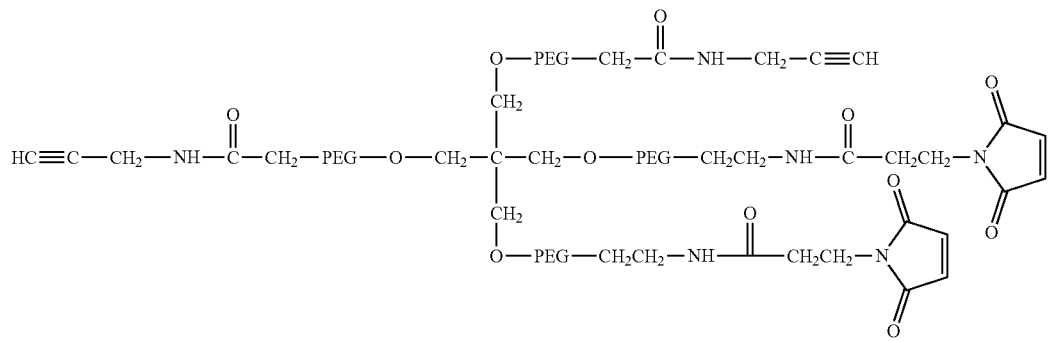

organic phase, dried with anhydrous sodium sulfate, filtered, concentrated to a viscous at 45° C., precipitated with 75 mL of diethyl ether, the precipitate was collected by filtration and dried under vacuum. The resulting 3.3 g of eight-arm polyethylene glycol-alkynyl-seven-acetic acid.

1H-NMR (DMSO) δ: 3.08 (s, —C≡CH, 1H), 4.01 (s, CH$_2$COOH, 14H)

Example 9

Preparation of Eight-Arm Polyethylene Glycol (10,000 Da)-Alkynyl-Seven Acetic Acid NHS Ester Weighed 1.0 g of eight-arm polyethylene glycol (10,000 da)-alkynyl-seven acetic acid and 0.12 g of n-hydroxy succinimide (NHS) and dissolved in 10 mL of methylene chloride, under nitrogen atmosphere, 0.23 g of N,N'-dicyclohexyl-carbodiimide (DCC) was added, reaction for 4 h, 0.35 g of maleic acid ethylenediamine was added, the reaction was allowed to proceed overnight protected from light, concentrated to dryness at 40° C., 20 mL of isopropanol was heated to dissolve and precipitated with an ice-water bath, filtered, washed the filter cake with isopropanol twice, dried under the vacuum to obtain eight-arm polyethylene glycol (10,000 da)-alkynyl-seven acetic acid MAL.

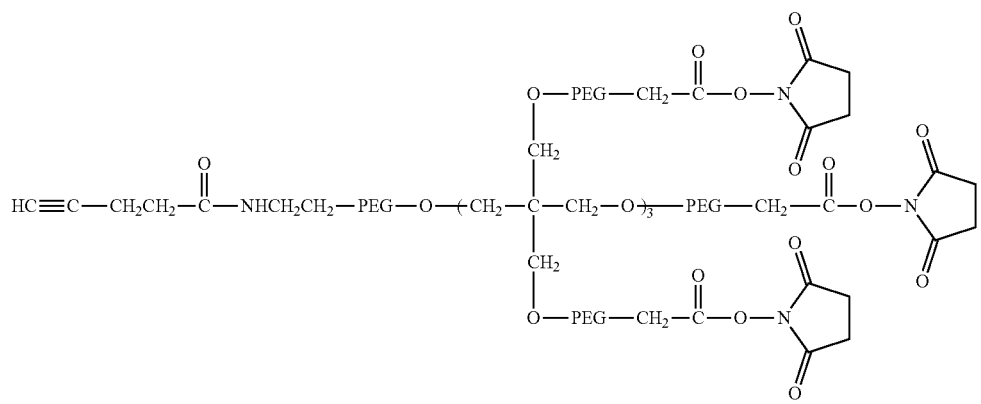

1.0 g of eight-arm polyethylene glycol (10,000 da)-mono-alkynyl-seven acetic acid and 0.12 g of N-hydroxy succinimide (NHS) were dissolved in 10 mL of methylene chloride, under nitrogen atmosphere, 0.23 g of N,N'-dicyclohexyl-carbodiimide (DCC) was added, a sealed reaction overnight, filtered, concentrated to dryness at 40° C., 20 mL of isopropanol was heated to dissolve and precipitated with an ice-water bath, filtered, washed the filter cake with isopropanol twice, dried under the vacuum to obtain eight-arm polyethylene glycol-mono-alkynyl-seven acetic acid NHS ester.

1H-NMR (DMSO) δ: 3.08 (s, —C≡CH, 1H), 4.6 (s, CH$_2$CO, 14H), 2.8 (s, CH$_2$ ring, 28H)

Example 10

Preparation of Eight-Arm Polyethylene Glycol (10,000 Da)-Alkynyl-Seven Acetic Acid MAL 1H-NMR (DMSO) δ: 3.08 (s, —C≡CH, 1H), 2.32 (t, CH$_2$N, 14H), 7.0 (s, CH ring, 14H)

Example 11

Preparation of Eight-Arm Polyethylene Glycol (20,000 Da)-Seven Alkynyl-Mono-Amine

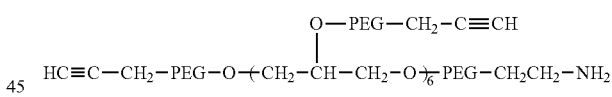

10.0 g of eight-arm polyethylene glycol (20,000 Da)-seven hydroxy-mono-ethyl amine was dissolved in 100 mL of methylene chloride, 0.077 mL of triethylamine was added, stirred for 10 minutes, 0.15 mL of di-tert-butyl

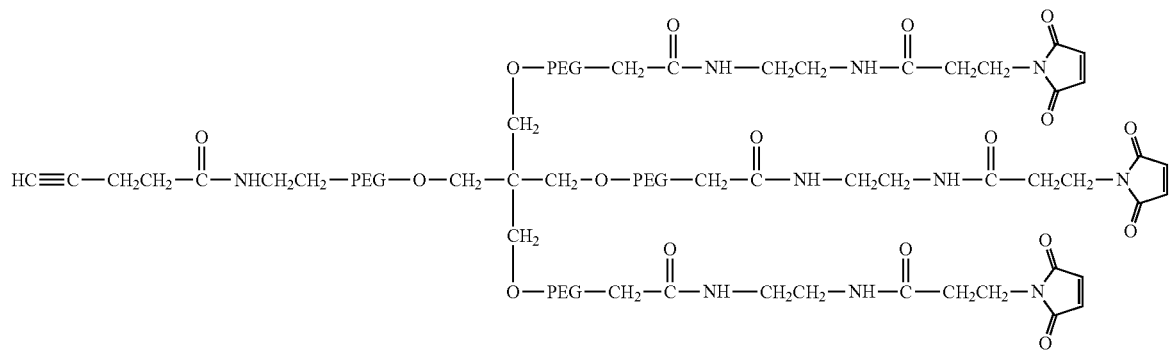

dicarbonate (Boc₂O) was added, reacted overnight at room temperature, concentrated at 40° C., precipitated with 100 mL of diethyl ether, filtered, dried under the vacuum to obtain 9.5 g of eight-arm polyethylene glycol (20,000 Da)-seven hydroxy-mono-Boc amide.

5.0 g of eight-arm polyethylene glycol (20,000 Da)-seven hydroxy-mono-BOC amide was dissolved in 100 mL of tetrahydrofuran, a nitrogen atmosphere for lowering the temperature to 0° C., 0.024 g of sodium hydride was added, reacted for 0.5 hours at room temperature, 1.12 mL of propargyl bromide (80% solution in toluene) was added, 0.0045 g of potassium iodide was added, heated to reflux for 2 hours protected from light, cooled, 50 mL of water was added, out of the tetrahydrofuran, extracted with methylene chloride for three times, dried with anhydrous sodium sulfate, filtered, concentrated, concentrated to a viscous at 45° C., precipitated with 100 mL of ethyl ether, the precipitate was collected by filtration and dried under vacuum. The resulting 3.9 g of eight-arm polyethylene glycol (20,000 Da)-seven propynyl-mono-BOC amide.

3.0 g of eight-arm polyethylene glycol (20,000 Da)-seven propynyl-mono-BOC amide was dissolved in 21 mL of methylene chloride, 9 mL of trifluoroacetic acid was added, reaction for 3 hours, concentrated at 40° C., precipitated with 60 mL of diethyl ether, filtered, dried under the vacuum to obtain 2.3 g of eight-arm polyethylene glycol (20,000 Da)-seven alkynyl-mono-ethyl amine.

1H-NMR (DMSO) δ: 3.08 (s, —C≡CH, 7H), 3.0 (m, CH₂N, 2H)

Example 12

Preparation of Eight-Arm Polyethylene Glycol (20,000 Da)-Seven Alkynyl-Mono-Ethyl Amine MAL azido derivatives (molecular weight of about 5,000) and 0.05 g of irinotecan-glycine hydrochloride salt were dissolved in 5 mL of water, 0.008 g of sodium ascorbate and 0.004 g of copper acetate were added, stirred for 25 minutes to form a gel at room temperature.

The above gel placed in a dialysis bag (throttle molecular weight of 5,000), washed with 20 mL of water for three times, until detecting no UV absorption in aqueous solution with high performance liquid chromatography (HPLC), put into a glass vial, 20 mL of water was added, shaken at 40° C. in thermostatic oscillatorthe, sampled at 30 min, 2 h, 4 h respectively, 0.0025 g/mL of irinotecan-glycine hydrochloride in water as the reference sample, measured the release amount of the gel at individual time points with high performance liquid chromatography.

The released ratio of Irinotecan-glycine is: 21% at 0.5 hour, 36% at 2 hours, 42% at 4 hours.

Example 14

Preparation of Four-Arm Polyethylene Glycol-Alkynyl (Molecular Weight of about 10,000) Gel and Drug Release Test In Vitro Thereof 0.25 g of four-arm polyethylene glycol-alkynyl (molecular weight of about 10,000), 0.25 g of polyethylene glycol-azido derivatives (molecular weight of about 10,000) and 0.05 g of irinotecan-glycine hydrochloride salt were dissolved in 5 mL of water, 0.004 g of sodium ascorbate and 0.002 g of copper acetate were added, stirred for 1 hour to form a gel at room temperature.

The above gel placed in a dialysis bag (molecular weight of 5,000), washed with 20 mL of water for three times, until detecting no UV absorption in aqueous solution with high performance liquid chromatography (HPLC), put into a

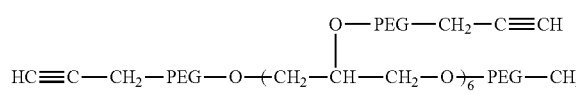
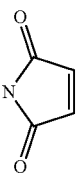

1.0 g of eight-arm polyethylene glycol (20,000 Da)-seven alkynyl-mono-ethyl amine was dissolved in 10 mL of methylene chloride, 0.017 g of 3-maleimidopropionic acid hydroxysuccinimide ester was added, reaction was allowed to proceed overnight protected from light, concentrated to dryness at 40° C., 20 mL of isopropanol was heated to dissolve and precipitated with an ice-water bath, filtered, washed the filter cake with isopropanol twice, dried under the vacuum to obtain eight-arm polyethylene glycol (20,000 Da)-seven alkynyl-mono-ethyl amine MAL.

1H-NMR (DMSO) δ: 3.08 (s, —C≡CH, 7H), 2.32 (t, CH₂N, 2H), 7.0 (s, CH ring, 2H)

Example 13

Preparation of Four-Arm Polyethylene Glycol-Alkynyl (Molecular Weight of about 5,000) Gel and Drug Release Test In Vitro Thereof 0.25 g of four-arm polyethylene glycol-alkynyl (molecular weight of about 5,000), 0.25 g of polyethylene glycol-glass vial, 20 mL of water was added, shaken at 40° C. in thermostatic oscillatorthe, sampled at 30 min, 2 h, 4 h respectively, 0.0025 g/mL of irinotecan-glycine hydrochloride in water as the reference sample, measured the release amount of the gel at individual time points with high performance liquid chromatography.

The released ratio of Irinotecan-glycine is: 35% at 0.5 hour, 54% at 2 hours, 69% at 4 hours.

Example 15

Preparation of Eight-Arm Polyethylene Glycol-Alkynyl (Molecular Weight of about 10,000) Gel and Drug Release Test In Vitro Thereof 0.25 g of eight-arm polyethylene glycol-alkynyl (molecular weight of about 10,000), 0.25 g of polyethylene glycol-azido derivatives (molecular weight of about 10,000) and 0.05 g of irinotecan-glycine hydrochloride salt were dissolved in 5 mL of water, 0.008 g of sodium ascorbate and 0.004 g of copper acetate were added, stirred for 10 min to form a gel at room temperature.

The above gel placed in a dialysis bag (having a throttle molecular weight of 5,000), washed with 20 mL of water for three times, until detecting no UV absorption in aqueous solution with high performance liquid chromatography (HPLC), put into a glass vial, 20 mL of water was added, shaken at 40° C. in thermostatic oscillatorthe, sampled at 30 min, 2 h, 4 h respectively, 0.0025 g/mL of irinotecan-glycine hydrochloride in water as the reference sample, measured the release amount of the gel at individual time points with high performance liquid chromatography.

The released ratio of Irinotecan-glycine is: 24% at 0.5 hour, 48% at 2 hours, 60% at 4 hours.

Examples 13-15 shows that, in the preparation of gel via a multi-arm polyethylene glycol-alkynyl derivatives reacted with other polyethylene glycol derivatives, the molecular weight and the number of branches of the polyethylene glycol can be used to affect or control the time of gel formation, the lower the molecular weight, the higher the number of the branch, the shorter the time of gel formation, and an increase in the branch number of poly ethylene glycol may be more effective in increasing the gel formation rate. At the same time, the molecular weight and the branch number also have a significant effect on the in vitro drug release time, therefore, to prepare a multi-arm polyethylene glycol-alkynyl derivatives can also be used to control the drug release sustaining process.

Example 16

Preparation of Four-Arm Polyethylene Glycol-Three Alkynyl-Dopamine and Gel Thereof

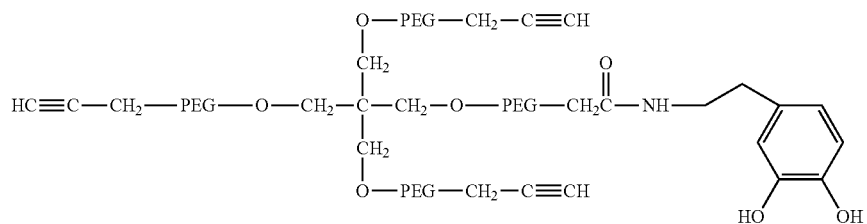

3.0 g of four-arm polyethylene glycol-propynyl-monoacetate NHS active ester (molecular weight of 5,000) was dissolved in 30 mL of methylene chloride, 0.12 g of dopamine and 0.11 mL of triethylamine were added, reaction was allowed to proceed overnight protected from light, concentrated to dryness at 40° C., 60 mL of isopropanol was heated to dissolve and precipitated with an ice-water bath, filtered, washed the filter cake with isopropanol twice, dried under the vacuum to obtain the four-arm polyethylene glycol-three-propynyl-dopamine.

1H-NMR (DMSO) δ: 3.08 (s, —C≡CH, 3H), 6.4 (m, ring, 1H), 6.6 (m, ring, 2H), 8.6 (s, OH, 1H), 8.7 (s, OH, 1H)

0.33 g of four-arm polyethylene glycol-three-propynyl-dopamine (having a molecular weight of about 5,000), 0.25 g of polyethylene glycol-azido derivatives (having a molecular weight of about 5,000) were dissolved in 6 mL of water, 0.008 g of sodium ascorbate and 0.004 g of copper acetate were added, stirred at room temperature for 30 minutes to form a gel.

The invention claimed is:

1. An alkynyl multi-arm polyethylene glycol active derivative having a structure of a general formula I or XVII

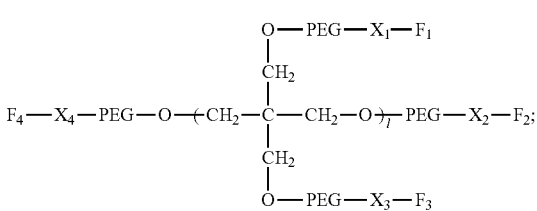

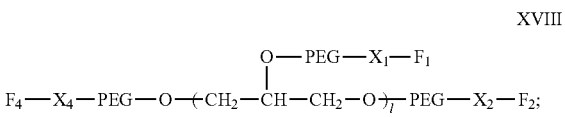

wherein:

PEG is the same or different —$(CH_2CH_2O)_m$—, m is an integer of average value of 3-250;

l is an integer ≥1;

$X_1$, $X_2$, $X_3$ and $X_4$ are linking groups independently selected from the group consisting of $C_{1-12}$ alkyl, aryl alkyl, ester group, carbonate group, amide group, amide ester group, ether group, and urethane group;

$F_1$, $F_2$, $F_3$ and $F_4$ are end groups independently selected from the group consisting of the following groups:

$NH_2$, —COOH, —$OCH_3$,

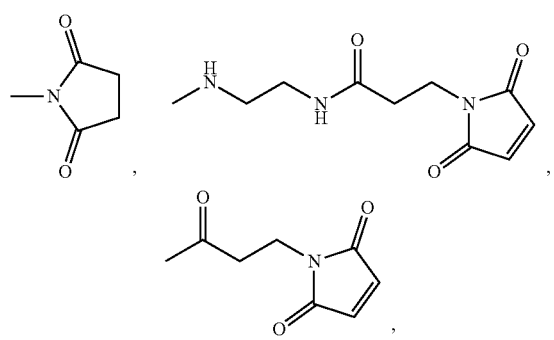

and —C≡CH, in the alkynyl multi-arm polyethylene glycol derivative of general formula I, only one or two or three of the $F_1$, $F_2$, $F_3$ and $F_4$ is (are) —C≡CH;

and in the alkynyl multi-arm polyethylene glycol derivative of general formula XVIII, only one or two of the $F_1$, $F_2$ and $F_4$ is (are) —C≡CH.

2. The alkynyl multi-arm polyethylene glycol active derivative of claim 1, wherein, the l is 1, 2, 3, 4, 5 or 6.

3. An alkynyl multi-arm polyethylene glycol active derivative having a structure of a general formula I or XVIII

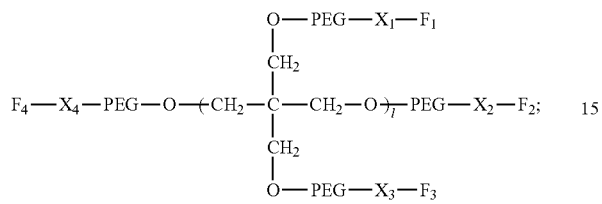

I

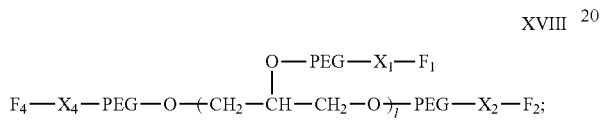

XVIII wherein:
PEG is the same or different —(CH$_2$CH$_2$O)$_m$—, m is an integer of average value of 3-250;
l is an integer ≥1;
$X_1$, $X_2$, $X_3$ and $X_4$ are independently selected from the group consisting of —(CH$_2$)$_i$—, —(CH$_2$)$_i$NHCO(CH$_2$)$_j$—, —(CH$_2$)$_i$CONH(CH$_2$)$_j$—, —(CH$_2$)$_i$NH—, —(CH$_2$)$_i$OCOO—, —(CH$_2$)$_i$OCONH—, —(CH$_2$)$_i$NHCOO—, —(CH$_2$)$_i$NHCONH—, —OC(CH$_2$)$_i$COO—, —(CH$_2$)$_i$COO—, —(CH$_2$)$_i$CONH; i is an integer of 1-10 in $X_1$, $X_2$, $X_3$ and $X_4$; j is an integer of 1-10 in $X_1$, $X_2$, $X_3$ and $X_4$;
$F_1$, $F_2$, $F_3$ and $F_4$ are end groups independently selected from the group consisting of the following groups:

NH$_2$, —COOH, —OCH$_3$,

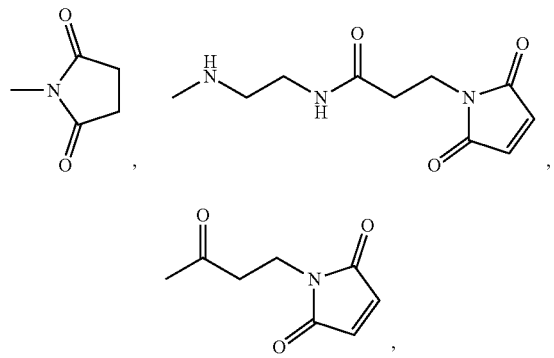

and —C≡CH,
in the alkynyl multi-arm polyethylene glycol derivative of general formula I, only one or two or three of the $F_1$, $F_2$, $F_3$ and $F_4$ is (are) —C≡CH;
and in the alkynyl multi-arm polyethylene glycol derivative of general formula XVIII, only one or two of the $F_1$, $F_2$ and $F_4$ is (are) —C≡CH.

4. The alkynyl multi-arm polyethylene glycol active derivative of claim 2, wherein, $X_1$, $X_2$, $X_3$ and $X_4$ are independently selected from the group consisting of —(CH$_2$)$_i$—, —(CH$_2$)$_i$NHCO(CH$_2$)$_j$—, —(CH$_2$)$_i$CONH (CH$_2$)$_j$—, i is 1, 2, 3, 4 or 5 in $X_1$, $X_2$, $X_3$ and $X_4$; and j is 1, 2, 3, 4 or 5 in $X_1$, $X_2$, $X_3$ and $X_4$.

5. The alkynyl multi-arm polyethylene glycol active derivative of claim 1, wherein, the multi-arm polyethylene glycol derivative has a molecular weight of 1,000-80,000 Da.

6. The alkynyl multi-arm polyethylene glycol active derivative of claim 5, wherein, the multi-arm polyethylene glycol derivative has a molecular weight of 3,000-20,000 Da.

7. An alkynyl multi-arm polyethylene glycol active derivative, wherein, having following general structure:

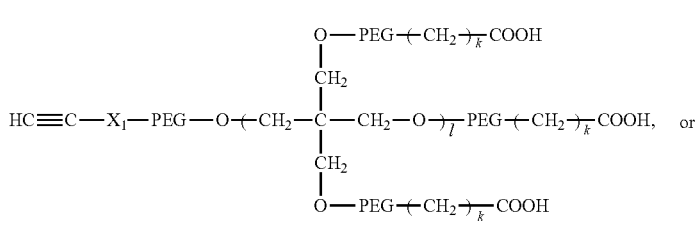

III

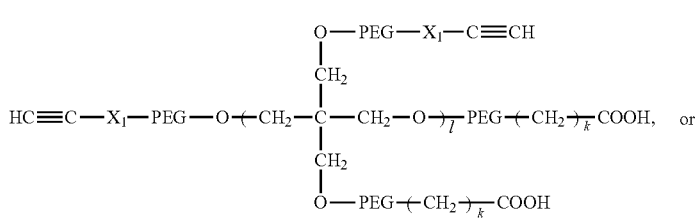

IV

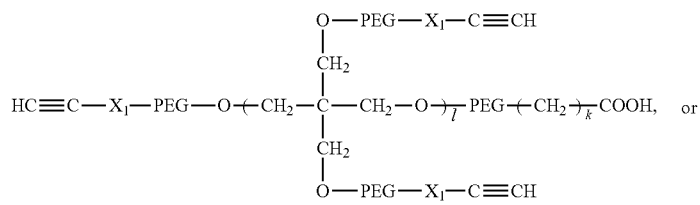
V
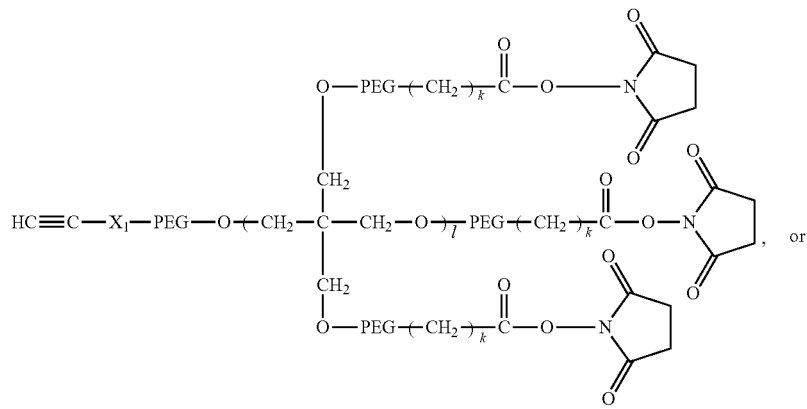
VI
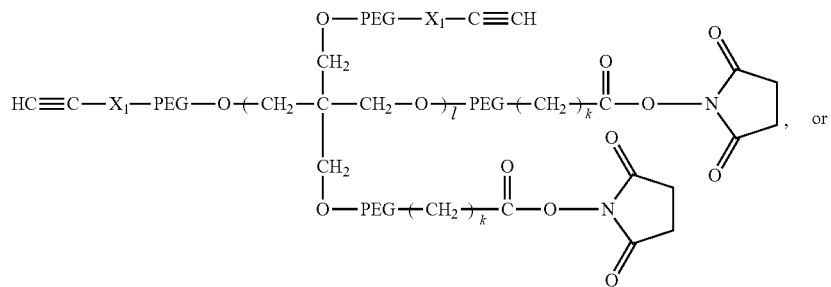
VII
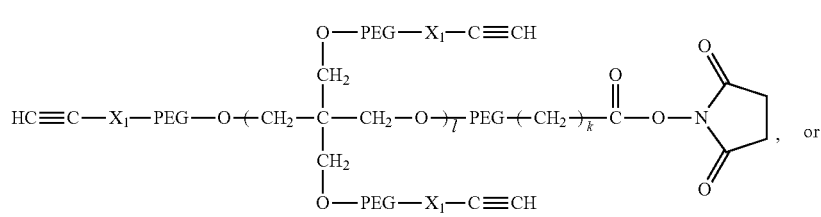
VIII
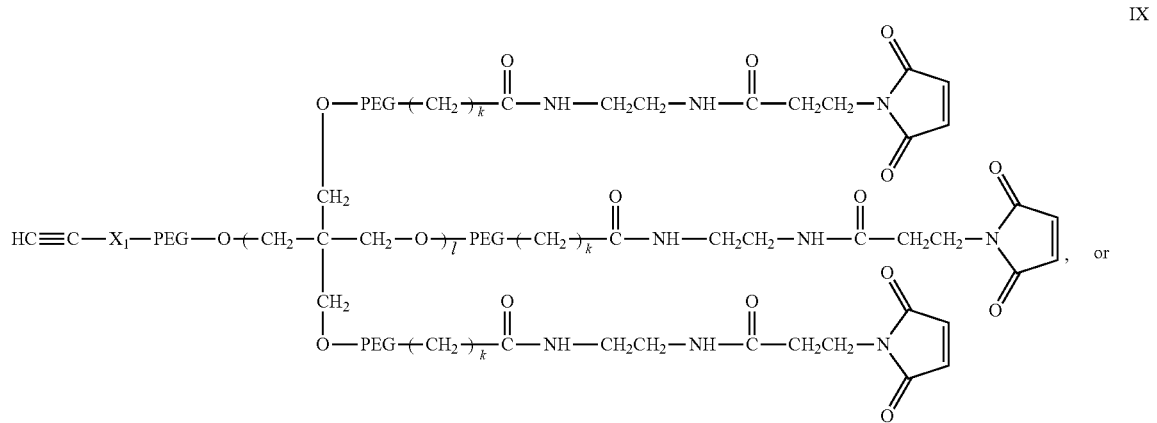
IX

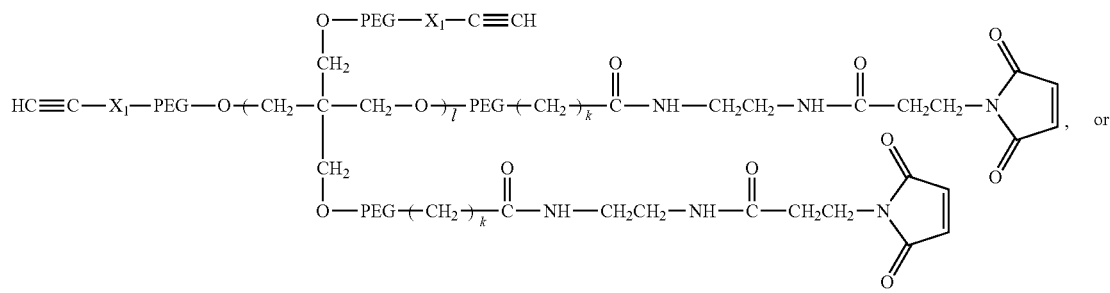
X
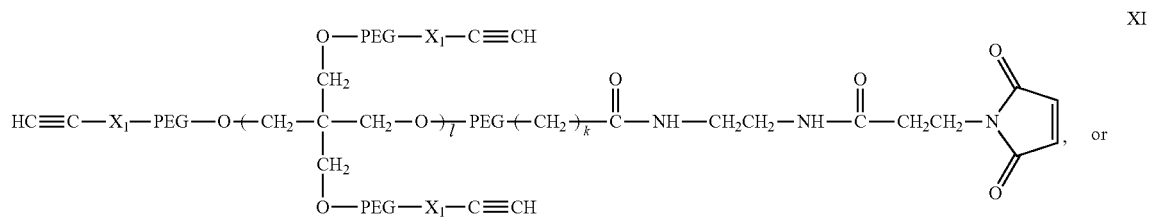
XI
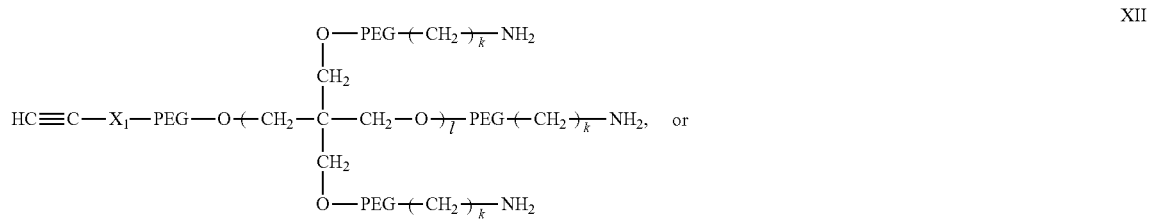
XII
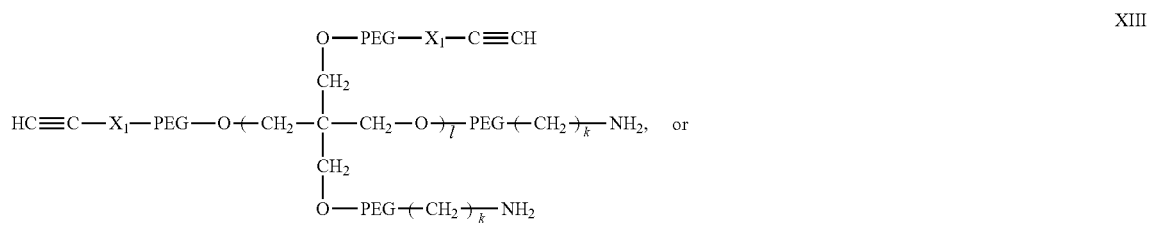
XIII
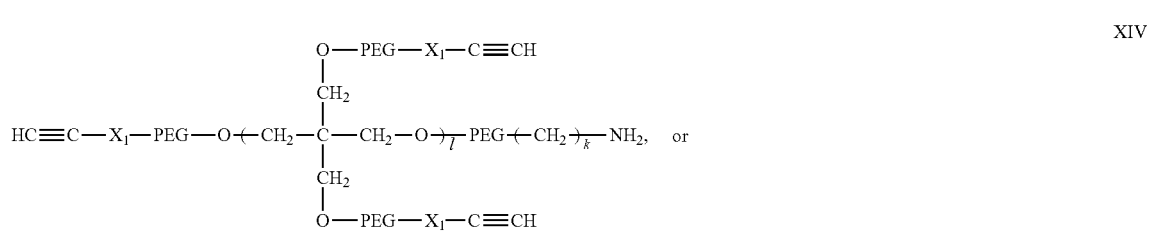
XIV
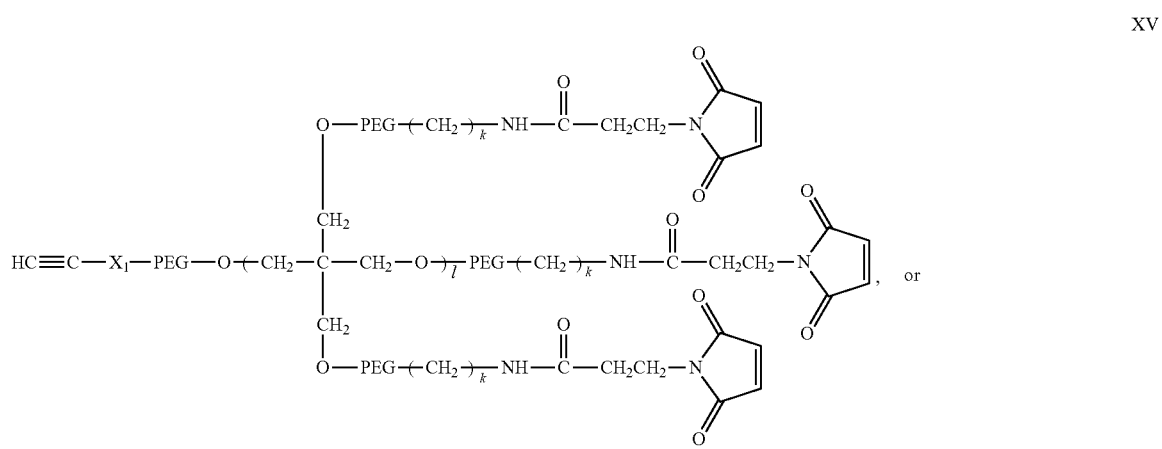
XV

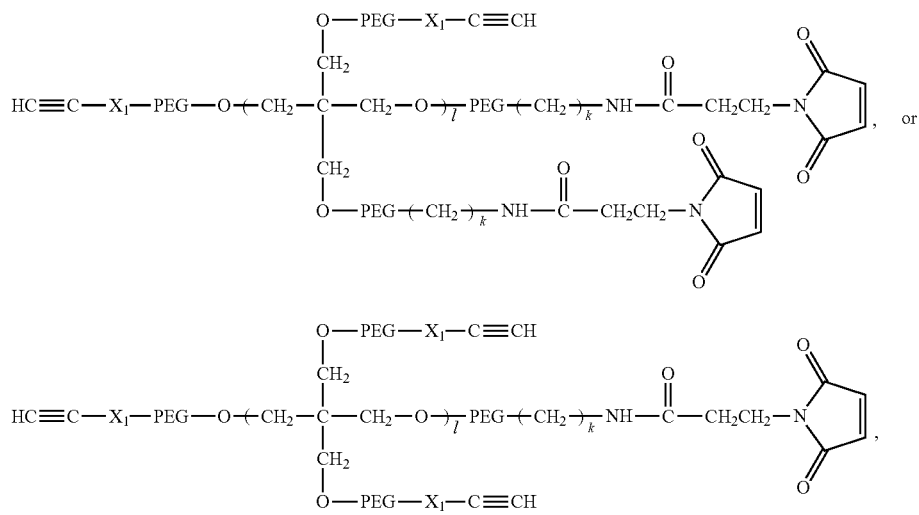

wherein:
PEG is the same or different —$(CH_2CH_2O)_m$—, m is an integer of average value of 3-250;
l is an integer ≥1;
$X_1$ is selected from of the groups consisting of —$(CH_2)_i$—, —$(CH_2)_i NHCO(CH_2)_j$—, —$(CH_2)_i CONH(CH_2)_j$—, —$(CH_2)_i NH$—, —$(CH_2)_i OCOO$—, —$(CH_2)_i OCONH$—, —$(CH_2)_i NHCOO$—, —$(CH_2)_i NHCONH$—, —$OC(CH_2)_i COO$—, —$(CH_2)_i COO$—, —$(CH_2)_i CONH$—; i is an integer of 1-10 in $X_1$; j is an integer of 1-10 in $X_1$;
and k is an integer of 1-10.

8. The alkynyl multi-arm polyethylene glycol active derivative of claim 7, wherein, $X_1$ is selected from the group consisting of —$(CH_2)_i$—, —$(CH_2)_i NHCO(CH_2)_j$—, and —$(CH_2)_i CONH(CH_2)_j$—, i is 1, 2, 3, 4 or 5 in $X_1$; and j is 1, 2, 3, 4 or 5 in $X_1$.

9. The alkynyl multi-arm polyethylene glycol active derivative of claim 7, wherein, k is 1, 2, 3, 4 or 5 in the alkynyl multi-arm polyethylene glycol active derivative.

10. The alkynyl multi-arm polyethylene glycol active derivative of claim 7, wherein, the alkynyl multi-arm polyethylene glycol derivative has a molecular weight of 1,000-80,000 Da.

11. The alkynyl multi-arm polyethylene glycol active derivative of claim 10, wherein, the alkynyl multi-arm polyethylene glycol derivative has a molecular weight of 3,000-20,000 Da.

12. A method of preparing the alkynyl multi-arm polyethylene glycol active derivative having a structure of a general formula I or XVIII of claim 1, wherein, comprising:
dissolving a multi-arm polyethylene glycol in a solvent, adding sodium hydride and reaction at room temperature, adding propargyl bromide and potassium iodide and reaction, obtaining a multi-arm polyethylene glycol-propynyl after separation;
or, dissolving a multi-arm polyethylene glycol-to-end acetic acid and N-hydroxy succinimide (NHS) in a solvent, adding N,N'-dicyclohexyl-carbodiimide and reaction, adding propargyl amine and reaction, obtaining a multi-arm polyethylene glycol-propynyl acetamide after separation;
or, dissolving a multi-arm polyethylene glycol-to-end hydroxyl-to-end acetic acid methyl ester in a solvent, adding sodium hydride and reaction at room temperature, adding propargyl bromide and potassium iodide and reaction, obtaining a multi-arm polyethylene glycol-propynyl-acetic acid methyl ester; hydrolyzing the multi-arm polyethylene glycol-propynyl-acetic acid methyl ester, obtaining a polyethylene glycol-propynyl-acetic acid derivative;
or, dissolving a multi-arm polyethylene glycol-to-end hydroxyl-to-end acetic acid methyl ester in a solvent, adding sodium hydride and reaction at room temperature, adding propargyl bromide and potassium iodide and reaction, obtaining a multi-arm polyethylene glycol-propynyl-acetic acid methyl ester; hydrolyzing the multi-arm polyethylene glycol-propynyl-acetic acid methyl ester, obtaining a polyethylene glycol-propynyl-acetic acid derivative; dissolving the polyethylene glycol-propynyl-acetic acid derivative in a solvent, adding N-hydroxy succinimide and N,N'-dicyclohexyl-carbodiimide and reaction, obtaining a multi-arm polyethylene glycol-propynyl-acetic acid NHS ester;
or, dissolving a multi-arm polyethylene glycol-to-end hydroxyl-to-end acetic acid methyl ester in a solvent, adding sodium hydride and reaction at room temperature, adding propargyl bromide and potassium iodide and reaction, obtaining a multi-arm polyethylene glycol-propynyl-acetic acid methyl ester; hydrolyzing the multi-arm polyethylene glycol-propynyl-acetic acid methyl ester, obtaining a polyethylene glycol-propynyl-acetic acid derivative; dissolving the polyethylene glycol-propynyl-acetic acid derivative in a solvent, adding N-hydroxy succinimide and N,N'-dicyclohexyl-carbodiimide and reaction, adding maleimido-ethylene-diamine and reaction, obtaining a multi-arm polyethylene glycol-to-end propynyl-to-end acetic acid MAL ester;
or, dissolving a multi-arm polyethylene glycol-to-end acetic acid-to-end ethyl amine in a solvent, adding triethylamine and di-tert-butyl dicarbonate and reaction, obtaining multi-arm polyethylene glycol-acetic acid-Boc amide; after the reaction, dissolving the multi-arm polyethylene glycol-acetic acid-Boc amide and N-hydroxy succinimide in a solvent, adding N,N'-dicyclohexyl-carbodiimide and reaction, adding propargyl amine and reaction, obtaining a multi-arm polyethylene glycol-alkynyl-Boc amide; dissolving the multi-arm polyethylene glycol-alkynyl-Boc amide in a solvent, adding trifluoro acetic acid and reaction, obtaining a multi-arm polyethylene glycol-to-end alkynyl-to-end ethyl amine;

or, dissolving a multi-arm polyethylene glycol-to-end acetic acid-to-end ethyl amine in a solvent, adding triethylamine and di-tert-butyl dicarbonate and reaction, obtaining a multi-arm polyethylene glycol-acetic acid-Boc amide; after the reaction, dissolving the multi-arm polyethylene glycol-acetic acid-Boc amide and N-hydroxy succinimide in a solvent, adding N,N'-dicyclohexyl-carbodiimide and reaction, adding propargyl amine and reaction, obtaining a multi-arm polyethylene glycol-alkynyl-Boc amide; dissolving the multi-arm polyethylene glycol-alkynyl-Boc amide in a solvent, adding trifluoro acetic acid and reaction, obtaining a multi-arm polyethylene glycol-to-end alkynyl-to-end ethyl amine; dissolving the multi-arm polyethylene glycol-to-end alkynyl-to-end ethyl amine in a solvent, adding 3-maleimidopropionic acid N-hydroxysuccinimide ester and reaction, obtaining a multi-arm polyethylene glycol-to-end alkynyl-to-end ethyl amine MAL.

* * * * *